United States Patent
Plishka et al.

(10) Patent No.: US 9,901,328 B2
(45) Date of Patent: Feb. 27, 2018

(54) VACUUM ASSISTED BIOPSY DEVICE

(75) Inventors: Michael Plishka, McGaw Park, IL (US); Evan Linderman, Northbrook, IL (US); John A. Krueger, Muskego, WI (US)

(73) Assignee: CAREFUSION 2200, INC., San Diego, CA (US)

( * ) Notice: Subject to any disclaimer, the term of this patent is extended or adjusted under 35 U.S.C. 154(b) by 0 days.

(21) Appl. No.: 13/490,075

(22) Filed: Jun. 6, 2012

(65) Prior Publication Data
US 2013/0331733 A1  Dec. 12, 2013

(51) Int. Cl.
*A61B 10/00* (2006.01)
*A61B 10/02* (2006.01)

(52) U.S. Cl.
CPC ...... *A61B 10/0283* (2013.01); *A61B 10/0275* (2013.01)

(58) Field of Classification Search
CPC ............ A61B 10/0283; A61B 10/0275; A61B 2010/0208
USPC .......................... 600/562, 564, 565, 566, 567
See application file for complete search history.

(56) References Cited

U.S. PATENT DOCUMENTS

| | | | | |
|---|---|---|---|---|
| 5,546,957 | A * | 8/1996 | Heske | 600/567 |
| 6,514,215 | B1 | 2/2003 | Ouchi et al. | |
| 6,620,111 | B2 * | 9/2003 | Stephens et al. | 600/567 |
| 6,702,761 | B1 * | 3/2004 | Damadian et al. | 600/576 |
| 6,955,653 | B2 * | 10/2005 | Eggers | 600/564 |
| 7,025,732 | B2 * | 4/2006 | Thompson et al. | 600/564 |
| 7,108,660 | B2 * | 9/2006 | Stephens et al. | 600/567 |
| 7,494,473 | B2 * | 2/2009 | Eggers et al. | 600/582 |
| 8,016,772 | B2 * | 9/2011 | Heske et al. | 600/566 |
| 8,052,614 | B2 * | 11/2011 | Heske et al. | 600/566 |
| 8,052,615 | B2 * | 11/2011 | Reuber et al. | 600/567 |
| 8,162,850 | B2 * | 4/2012 | Parihar et al. | 600/565 |
| 8,206,316 | B2 * | 6/2012 | Hibner et al. | 600/567 |
| 8,206,409 | B2 * | 6/2012 | Privitera et al. | 606/167 |
| 8,267,868 | B2 * | 9/2012 | Taylor et al. | 600/564 |
| 8,277,394 | B2 * | 10/2012 | Hibner | 600/568 |
| 8,282,574 | B2 * | 10/2012 | Coonahan et al. | 600/564 |
| 8,283,890 | B2 * | 10/2012 | Videbaek | 320/115 |
| 8,337,415 | B2 * | 12/2012 | Trezza et al. | 600/567 |
| 8,376,957 | B2 * | 2/2013 | Hibner et al. | 600/566 |

(Continued)

FOREIGN PATENT DOCUMENTS

| | | |
|---|---|---|
| EP | 1 889 573 A1 | 2/2008 |
| EP | 1 932 481 A1 | 6/2008 |
| WO | WO 2006/005344 A1 | 1/2006 |

OTHER PUBLICATIONS

Supplementary European Search Report of related European Patent Application No. 13800819.8 dated Feb. 17, 2016.

*Primary Examiner* — Daniel Cerioni
(74) *Attorney, Agent, or Firm* — Arent Fox LLP

(57) ABSTRACT

Methods and devices for providing a biopsy device with a modified handle and stylet that provides a vacuum to be delivered to the targeted tissue for removal. The vacuum may draw the tissue into the notch where the tissue may then be severed via the cannula. Alternatively, the tissue may be drawn into to the notch after being severed via the stylet and/or cannula. The vacuum may be used to bring a larger amount of tissue into the notch than would otherwise be brought in the notch if no vacuum was used, providing a larger sample through the same size access point.

15 Claims, 11 Drawing Sheets

(56) References Cited

U.S. PATENT DOCUMENTS

| | | |
|---|---|---|
| 8,430,824 B2* | 4/2013 | Videbaek et al. ............ 600/562 |
| 2003/0229293 A1 | 12/2003 | Hibner et al. |
| 2006/0074345 A1* | 4/2006 | Hibner ......................... 600/566 |
| 2006/0129063 A1* | 6/2006 | Thompson et al. .......... 600/566 |
| 2007/0032740 A1 | 2/2007 | Quick et al. |
| 2007/0032741 A1* | 2/2007 | Hibner et al. ................ 600/566 |
| 2007/0032742 A1* | 2/2007 | Monson et al. .............. 600/566 |
| 2007/0032743 A1* | 2/2007 | Hibner ......................... 600/566 |
| 2007/0106176 A1 | 5/2007 | Mark et al. |
| 2007/0149895 A1* | 6/2007 | McCullough et al. ....... 600/566 |
| 2008/0045860 A1* | 2/2008 | Miller et al. ................. 600/567 |
| 2008/0146965 A1* | 6/2008 | Privitera et al. ............. 600/567 |
| 2008/0306406 A1* | 12/2008 | Thompson et al. .......... 600/566 |
| 2009/0105609 A1* | 4/2009 | Thompson et al. .......... 600/566 |
| 2009/0198149 A1* | 8/2009 | Privitera et al. ............. 600/566 |
| 2009/0204024 A1* | 8/2009 | Miller .......................... 600/567 |
| 2010/0113971 A1* | 5/2010 | Hibner ......................... 600/564 |
| 2010/0280367 A1* | 11/2010 | Ducharme et al. .......... 600/426 |
| 2010/0312140 A1* | 12/2010 | Smith et al. .................. 600/566 |
| 2011/0082387 A1* | 4/2011 | Miller et al. ................. 600/567 |
| 2011/0087131 A1* | 4/2011 | Videbaek ..................... 600/567 |
| 2011/0144532 A1* | 6/2011 | Monson et al. .............. 600/566 |
| 2011/0144533 A1* | 6/2011 | Chudzik et al. ............. 600/567 |
| 2011/0152716 A1* | 6/2011 | Chudzik et al. ............. 600/567 |
| 2012/0059247 A1* | 3/2012 | Speeg et al. ................. 600/424 |
| 2012/0095366 A1* | 4/2012 | Heske et al. ................. 600/566 |
| 2012/0130275 A1* | 5/2012 | Chudzik et al. ............. 600/567 |

* cited by examiner

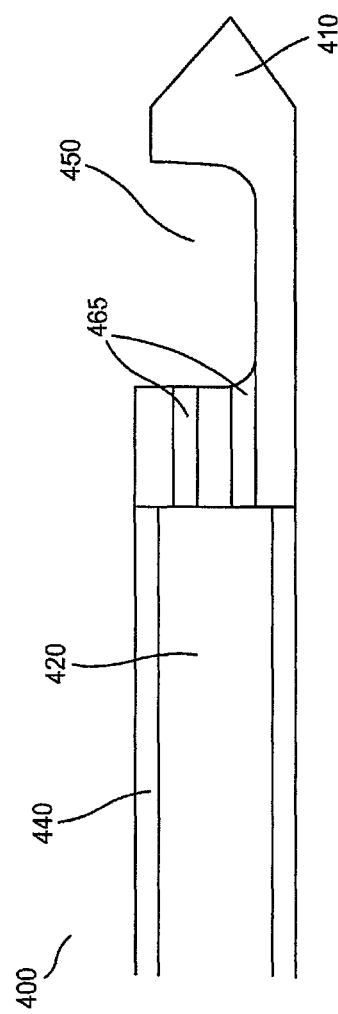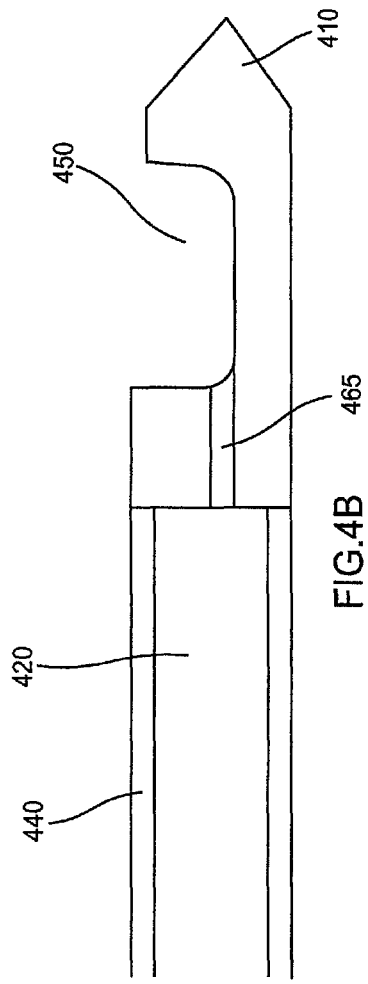

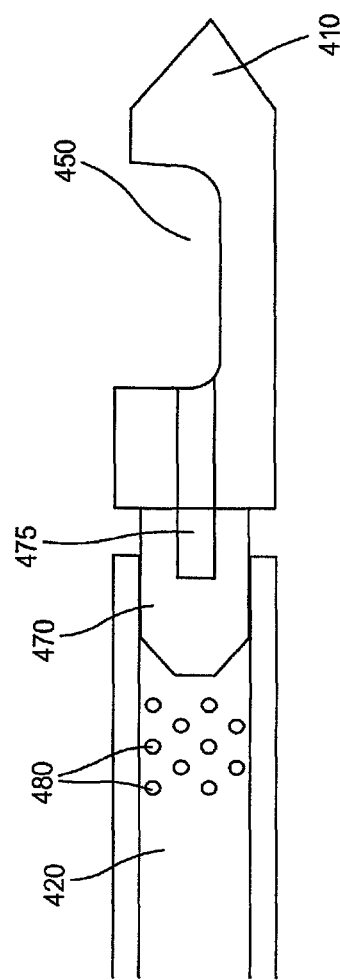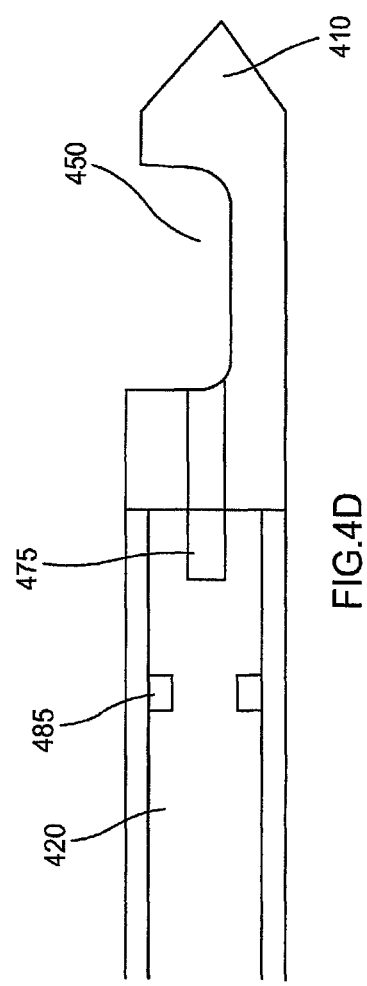

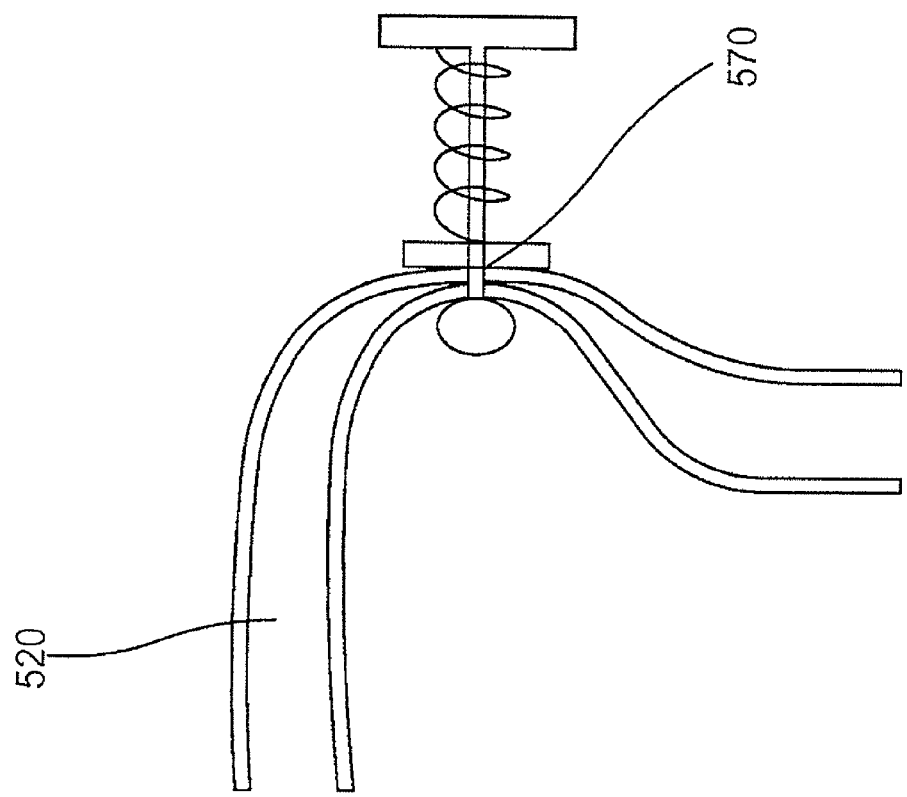

VACUUM ASSISTED BIOPSY DEVICE

BACKGROUND OF THE INVENTION

1. Field of Invention

Aspects of the present invention relate to methods and devices for performing vacuum assisted biopsies. More particularly, aspects of the current invention relate to methods and devices for performing vacuum assisted spring-loaded biopsies.

2. Description of Related Art

A variety of biopsy devices having sampling needles as part of their structure are available in the medical field. Typical biopsy devices include those that are designed to obtain samples from hard tissues, such as bone, and those that are designed for sampling of softer tissues. Soft tissue biopsy devices can include a structure whereby a sampling needle resides within an outer cannula and moves relative thereto during sampling. In particular, the operation of the device involves extending the distal end of the sampling needle beyond the distal end of the outer cannula to expose and introduce a portion of the needle to the tissue sampling site.

For example, U.S. Pat. No. 7,018,343 describes a spring-loaded biopsy device, described herein with respect to FIGS. 1A-1B. The biopsy device 20 is illustrated in FIG. 1A, the biopsy device 20 having a rapid firing mechanism within (not shown), which can include typical components that can be found in such devices, such as a handle portion 21 housing the operative mechanism components (not shown), loading and trigger component 22, outer cannula 23 and biopsy needle 2 partially residing within the outer cannula 23 with the distal end portion of the needle 2 exposed. Such biopsy devices can contain parts, e.g., the handle portion and loading and trigger component, composed of conventional materials, such as plastic or metallic materials. A profile of the needle 2 extending from the cannula 23 is illustrated in FIG. 1B, where the needle 2 includes a notch configured to collect tissue samples.

However, the samples obtained by the above devices generally do not fill the entire space enclosed in the notch within the biopsy device, and the collected samples are not as large as they could possibly be, which could sometimes lead to inaccurate diagnoses obtained from the sample.

There is a need in the art, therefore, for biopsy devices capable of obtaining samples that fill the entire space enclosed in the notch and that ensure the collected samples are as large and contiguous as possible.

SUMMARY OF THE INVENTION

In light of the above described problems and unmet needs, aspects of the current invention provide biopsy systems and devices with a modified handle and stylet through which a vacuum is delivered to the targeted tissue prior to being severed by a cannula for removal. The biopsy needle, which is capable of penetrating skin and/or tissue to collect biopsy samples, may include a pointed stylet. A distal portion of the stylet may include a notch capable of receiving tissue that has been severed by the cutting cannula. According to various aspects, the vacuum may draw the sample into the notch to fill a larger amount of the notch, after which the tissue may be severed via the cannula. Alternatively, the tissue that is severed via the stylet and the cannula may be deposited within the notch, and the vacuum may be used to maintain the severed tissue within the notch while the biopsy device is extracted from the body of the patient. For example, the vacuum may be used to draw a larger amount of tissue into the notch than would otherwise be collected in the notch if no vacuum was used before the tissue sample is severed by the biopsy device, thus providing a larger sample through the same size access point within the patient.

According to various aspects, the vacuum also provides more assurance that the desired tissue is captured by clinician. Diseased tissue has varied densities when compared to non-diseased tissue, and the use of vacuum to pull the tissue of various densities into the notch provides clinical advantages compared to biopsy needles without vacuum. In addition, vacuum can be applied to needles of very small gauges, which results in improving the biopsy procedure with respect to smaller lesions or calcifications.

There are many benefits of using a spring loaded cannula in combination with vacuum assistance. For example, the cannula provides a sharp cutting edge that cleanly severs the tissue within the notch in a fraction of second. The weight and size of the device are also clinical aspects of the proposed invention because the clinician needs to position the tip of the notch in exactly the right location, which is typically done under ultrasound, and once the tip is placed, the clinician needs to manipulate the stylet tip and vacuum in order to maximize the clinical benefit. The size and weight of the device generally hinder the ability of the clinician to position the biopsy device in the desired location. The visibility of the device under ultrasound is also a clinical factor. Markings on the tip of the stylet, including a small grove around the entire diameter of the stylet, may provide significant improvements of the visibility of the stylet tip from any direction with respect to the ultrasound probe. According to various aspects, surface texturing also improves the overall image.

According to various aspects, the vacuum applied to the biopsy device may be controlled and provided in a variety of ways in order to ensure adequate suction of the tissue into the notch of the stylet of the biopsy device. The vacuum may be controlled by restricting flow through a valve mechanism where the clinician can control the total amount of vacuum being applied. Alternatively, the device may provide the clinician with the ability to turn on or off the vacuum at a predetermined level. According to various aspects, both options may provide varying clinical advantages depending on the type of tissue being biopsied, the size of the lesion or calcification, and the presence of potential clinical complications such as blood vessels, bone, membranes, etc. According to various aspects, the size of the vacuum pump, location of the trigger and amount of vacuum may also be clinically relevant. The pump can be small enough to fit within the clinician's hand or to stand alone on the table. Typical battery powered pumps may provide cost effective benefits to using vacuum as an assist for spring loaded biopsy devices.

Additional advantages and novel features of these aspects of the invention will be set forth in part in the description that follows, and in part will become more apparent to those skilled in the art upon examination of the following or upon learning by practice of the invention.

BRIEF DESCRIPTION OF THE DRAWINGS

Various example aspects of the systems and methods will be described in detail, with reference to the following figures, wherein:

FIGS. 4A-4D are diagrams illustrating a communication between the cannula and the notch in a vacuum-assisted biopsy device, according to various aspects of the current invention; and FIGS. 5A-5B are diagrams illustrating vacuum valves in a vacuum-assisted biopsy device, according to various aspects of the current invention.

DETAILED DESCRIPTION

These and other features and advantages of this invention are described in, or are apparent from, the following detailed description of various example aspects.

Figures 1A, 1B:
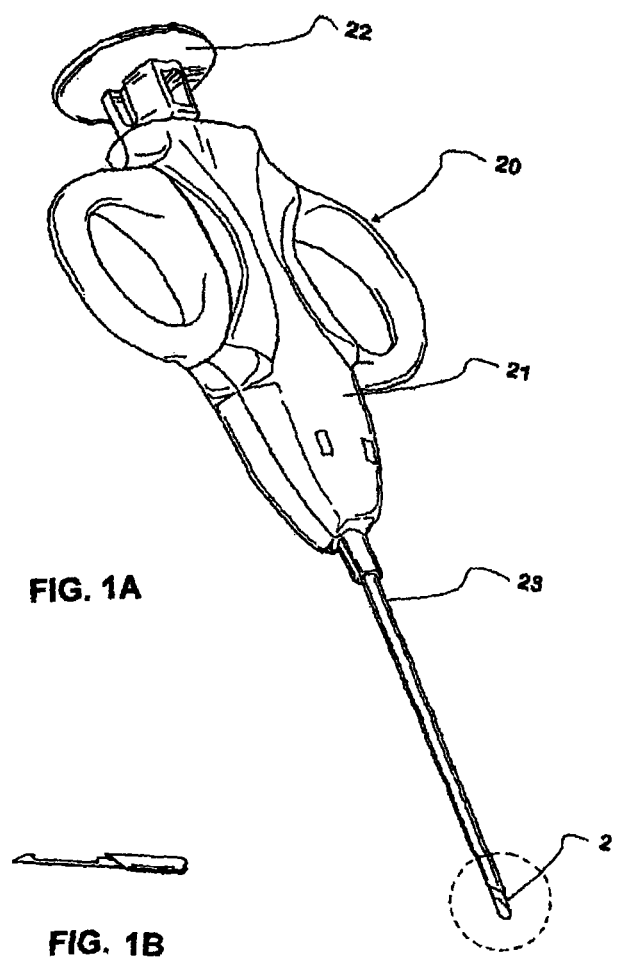
FIGS. 1A-1B illustrate a conventional spring-loaded biopsy device.
Figure 2A:
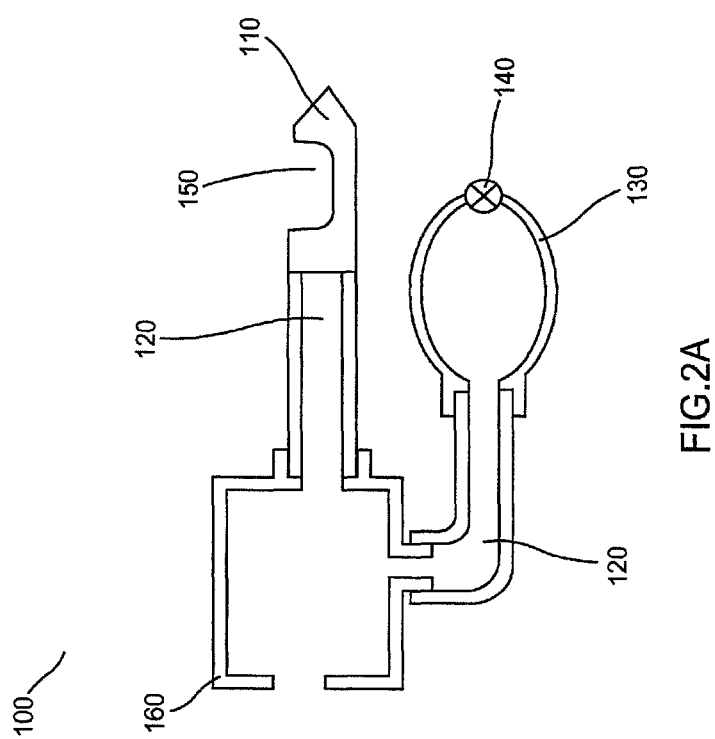
FIGS. 2A-2B are diagrams illustrating a vacuum-assisted biopsy device, according to various aspects of the current invention.
Figure 2B:
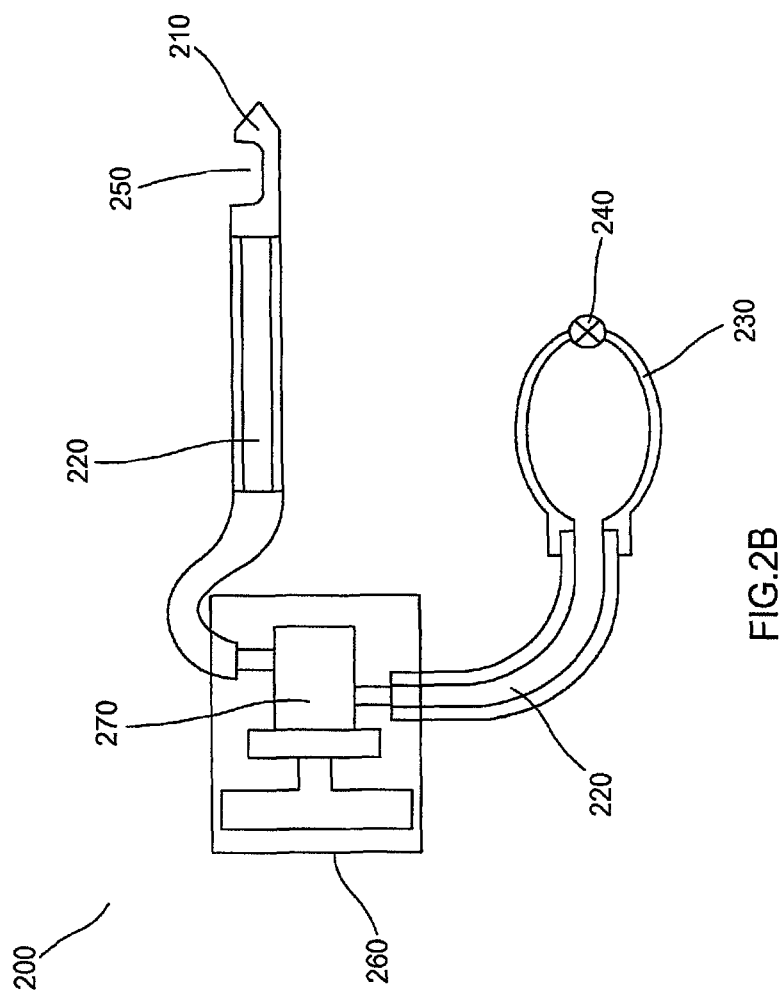

FIGS. 2A-2B are diagrams illustrating a vacuum-assisted biopsy device, according to various aspects of the current invention. In FIG. 2A, the vacuum-assisted biopsy device 100 includes a stylet tip 110 that, during operation, penetrates the skin/tissue of a patient and is inserted through the skin to remove one or more tissue samples from the patient, the tissue samples being deposited in the notch 150 of the stylet tip 110. According to various aspects, the stylet tip 110 may be connected to a vacuum pump 130 via a vacuum line 120 and a housing 160, the vacuum pump 130 including a valve 140. The housing 160 may include, in the case of a spring-loaded biopsy device, a valve mechanism and/or the firing mechanism to fire a cannula over the stylet tip 110 to sever tissue samples. According to various aspects, the housing 160 may also be used as a handle by an operator to operate the biopsy device. The valve 140 may, for example, only allow flow in a single direction such that air can only flow out of the vacuum pump 130 via the valve 140, thus creating a vacuum. In addition, the valve 140 may help prevent foreign materials from coming in contact with the target tissue.

In operation, the vacuum pump 130 may create a vacuum and transmit the vacuum via the vacuum line 120 to the stylet tip 110. Accordingly, when the stylet tip 110 penetrates the skin/tissue of the patient, the vacuum provided through the vacuum line 120 may draw an amount of tissue in the notch 150 that is larger than if no vacuum was provided, and the tissue sample may then be severed via, for example, firing a cutting cannula. Alternatively, the tissue sample that is first severed via the stylet tip 110 may be deposited in the notch 150, and the vacuum may be used to maintain the severed tissue sample within the notch 150 while the biopsy device is extracted from the body of the patient. As a result, when the stylet tip 110 is removed from the body of the patient, larger tissue samples can be collected by the biopsy device 100 because of the action of the vacuum that maintains a large amount of tissue inside the notch 150.

In FIG. 2B, the vacuum-assisted biopsy device 200 includes a stylet tip 210 that is to be inserted within the body of a patient during a biopsy so that tissue sample(s) from the patient may be deposited in the notch 250 of the stylet tip 210. According to various aspects, the stylet tip 210 may be connected to a vacuum pump 230 via a vacuum line 220, the vacuum pump 230 including a valve 240. The housing 260 may include, in the case of a spring-loaded biopsy device, a valve mechanism such valve assembly 270 and/or the firing mechanism to fire a cannula over the stylet tip 210 to sever tissue samples. According to various aspects, the housing 260 may also be used as a handle by an operator to operate the biopsy device. The valve 240 may, for example, only allow flow in a single direction such that air can only flow out of the vacuum pump 230 via the valve 240. As such, the valve 240 may help prevent foreign materials from coming in contact with the target tissue. In operation, the vacuum pump 230 may create a vacuum and transmit the vacuum via the vacuum line 220 to the stylet tip 210. Furthermore, an additional valve assembly 270 may be introduced between the stylet tip 210 and the vacuum pump 230 in order to regulate the vacuum flow between the stylet tip 210 and the pump 230. According to various aspects, the valve assembly 270 may be in a closed state, where no vacuum is communicated to the stylet tip 210, or in an open state, where a vacuum is communicated to the stylet tip 210.

In operation, the vacuum pump 230 may create a vacuum and may transmit the vacuum via the vacuum line 220 to the stylet tip 210 via the additional valve 270. Accordingly, when the stylet tip 210 penetrates the skin of the patient, the vacuum provided through the vacuum line 220 may draw an amount of tissue in the notch 250 that is larger than if no vacuum was provided, and the tissue may then be severed via, for example, firing a cutting cannula. Accordingly, a larger amount of tissue sample may be collected in the notch 250 of the biopsy device 200 as compared to a biopsy performed without vacuum.

Figure 3A:
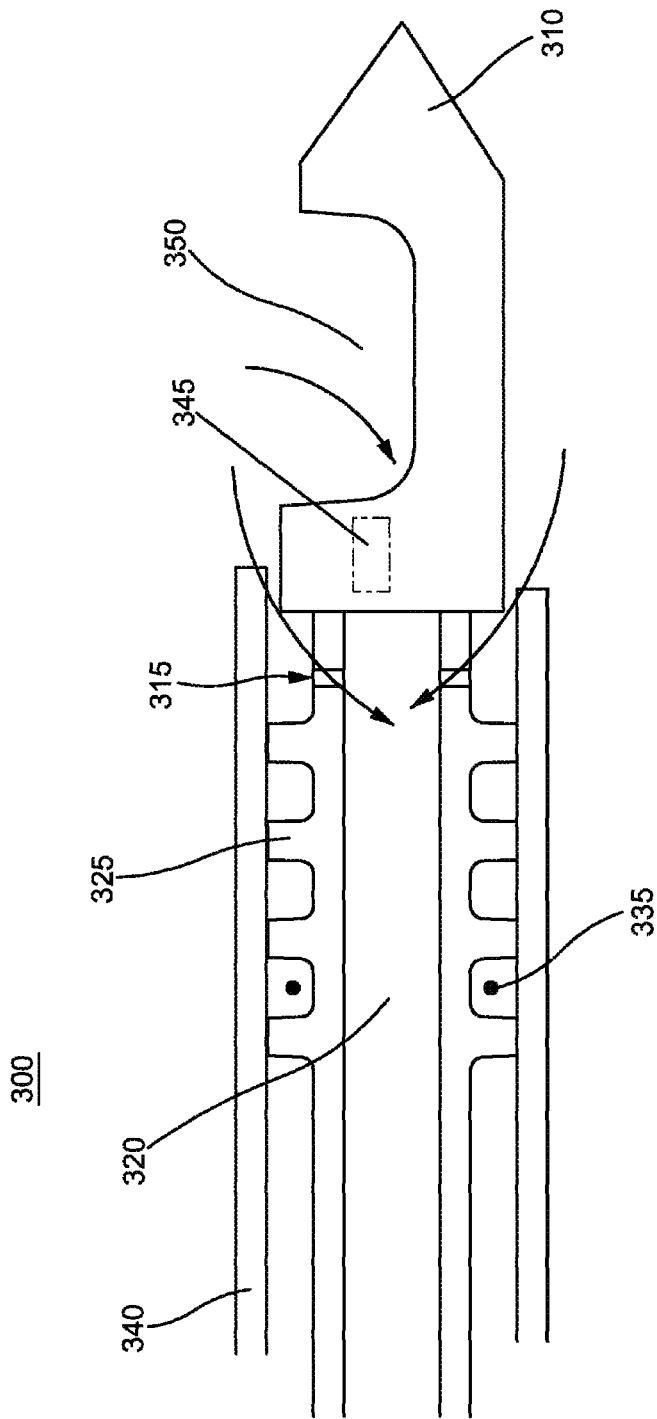
FIGS. 3A-3D are diagrams illustrating a cannula and notch in a vacuum-assisted biopsy device, according to various aspects of the current invention.

FIGS. 3A-3D are diagrams illustrating a cannula and stylet having a notch in a vacuum-assisted biopsy device, according to various aspects of the current invention. In FIG. 3A, the biopsy device 300 includes the stylet tip 310 having the notch 350 connected to the vacuum line 320, for example, via conduit 345 providing an air/vacuum communication between the notch 350 and the vacuum line 320, thereby providing a travel path of the suction action of the vacuum. According to various aspects, the vacuum line 320 may include one or more outlets or passageways 315 that may allow for vacuum to flow between the vacuum line 320 and the environment during vacuum actuation by the vacuum pump. As such, when vacuum is applied and transmitted from the vacuum line, the tissue that has been severed, or that is about to be severed, by the cannula 340 may be attracted to the notch 350 via a vacuum travelling along the three arrows depicted in FIG. 3A and representative of the travel path of the suction action of the vacuum. As a result, a large amount of tissue may be attracted to the notch 350 which can be severed and extracted by the biopsy device 300.

According to various aspects, the circumference of the body of the stylet, which may correspond to a back portion of the stylet tip 310 and which is typically covered by the cannula 340, may be altered such as to provide enough space for the vacuum to travel inside the cannula and around the outer surface of the stylet. For example, portions of the circumference of the stylet may be machined away so as to leave an uneven cylindrical shape with enough space to allow circulation of vacuum or air around the circumference of the stylet.

According to various aspects, the outside surface 325 of the vacuum line 320 may include asperities and other surface features to provide, for example, space for a lubricant to provide adequate lubrication during insertion and operation of the biopsy device. In addition, the lubricant may prevent a vacuum leak during operation of the biopsy device. According to various aspects, the outside surface 325 of the vacuum line 320 may also be covered with a lubricant 335 such as, e.g., silicone grease, to facilitate movement of the stylet tip 310 and the vacuum line 320 inside the wall of the outer tube or cannula 340 of the biopsy device 300, and thus to facilitate movement of the stylet tip 310 in and out of the outer tube or cannula 340 to penetrate the skin/tissue of the patient, to remove tissue sample(s), or to rotate inside the outer tube or cannula 340 to remove tissue sample(s). In addition, the lubricant 335 may also act as a vacuum membrane to prevent vacuum from escaping through other portions of the biopsy device 300 and to constrain the path of the vacuum to the paths shown in FIG. 3A by the three arrows.

Figure 3B:
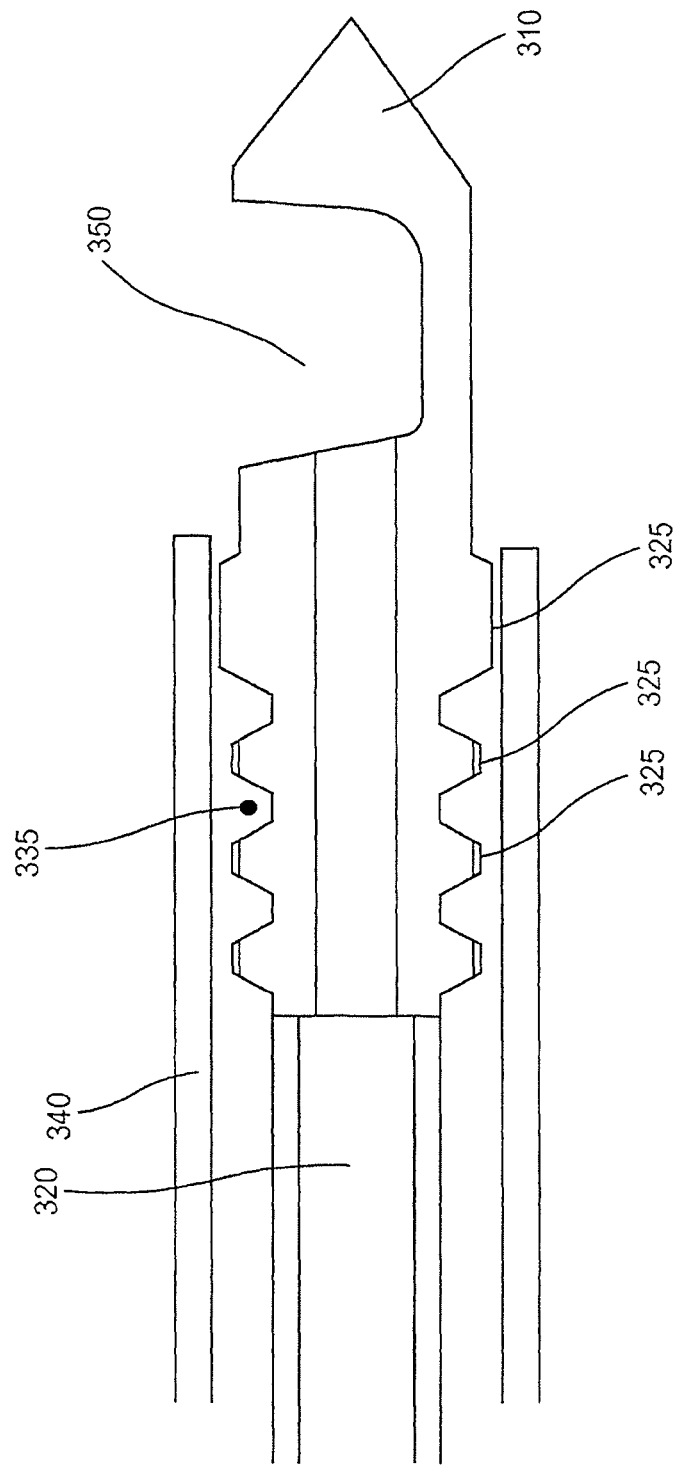

In FIG. 3B, the biopsy device 300 includes the stylet tip 310 having the notch 350 connected to the vacuum line 320. According to various aspects, the outside surface of the vacuum line 320 may have surface features 325 of various sizes to provide, for example, space for adequate lubrication of the stylet tip 310 during insertion and operation of the biopsy device, and the surface features 325 may be configured to fit against the inner wall of the outer tube or cannula 340 of the biopsy device. In addition, grooves 335 may also be provided on the surface of the stylet tip 310 between the surface features 325 to receive, for example, lubricant 335 to facilitate movement and/or rotation of the stylet tip 310 inside the outer tube or cannula 340 and to provide a vacuum membrane.

Figure 3C:
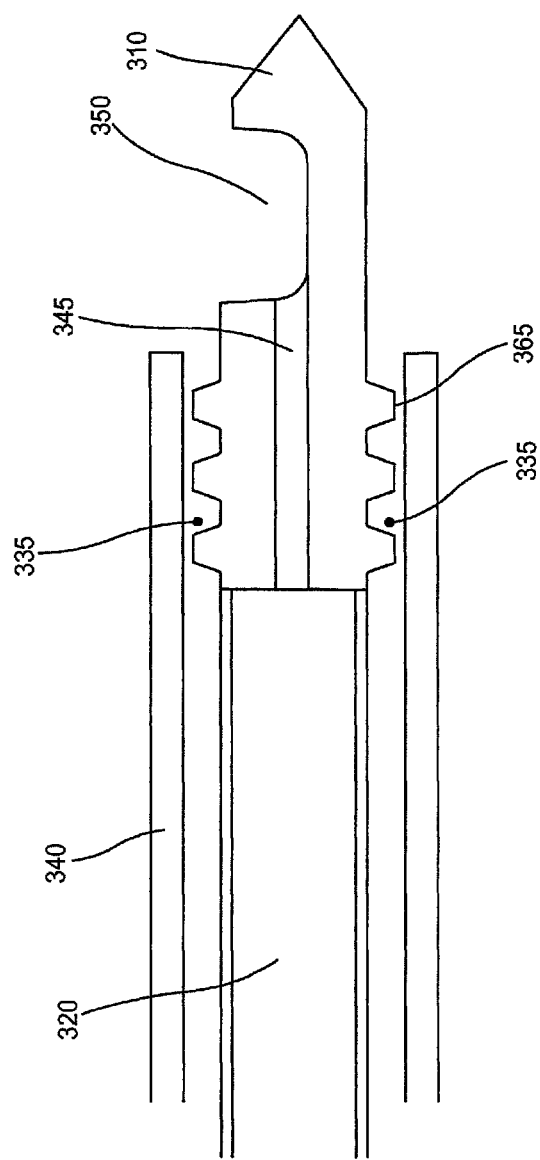

FIG. 3C illustrates another aspect of the current invention, where a conduit 345 provides an air/vacuum communication between the notch 350 and the vacuum line 320. Accordingly, the vacuum provided via the vacuum line 320 can be transmitted to the notch 350 and can attract an amount of tissue sample into the notch 350 either before the tissue is severed, or after the tissue has been severed.

Figure 3D:
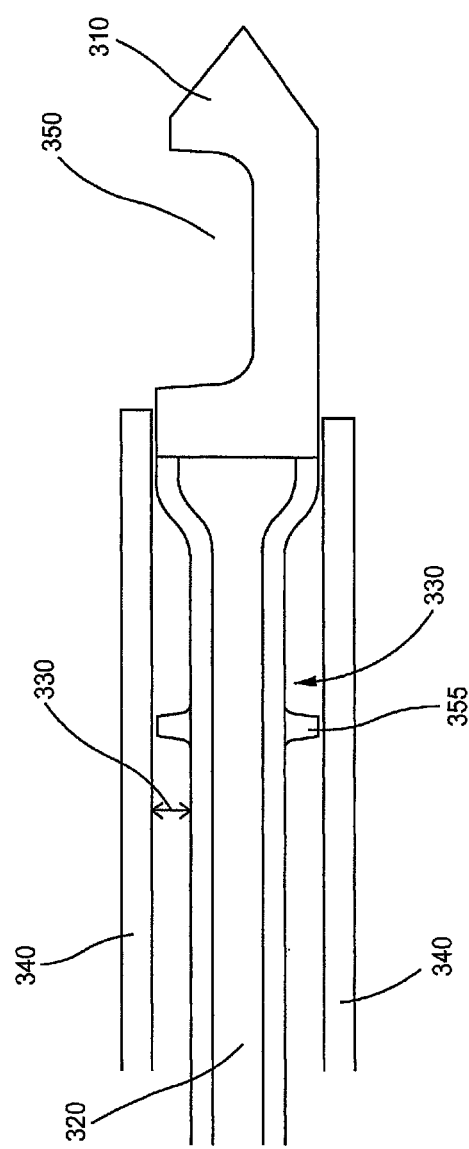

In FIG. 3D, according to various aspects of the current invention, a friction space or clearance 330 may be provided between the vacuum line 320 and the outer tube or cannula 340 to allow the stylet tip 310 and the vacuum line 320 to move and rotate freely inside the outer tube or cannula 340, resulting in the outside diameter of the vacuum line 320 being smaller than the inside diameter of the outer tube or cannula 340 by an amount sufficient to reduce the friction between the outer tube or cannula 340 and the vacuum line 320. For example, the clearance between the outside diameter of the vacuum line 320 and the inside diameter of the outer tube or cannula 340 may be in the range of 0.015". According to various aspects, an asperity 355 may also be provided on the outside surface of the vacuum line 320 to maintain, for example, the clearance 330 between the vacuum line 320 and the outer tube or cannula 340 at a constant value, and may provide space for inserting a lubricant to reduce friction between the vacuum line 320 and the cannula 240 and to also provide sealing of the space between the vacuum line 320 and the cannula 240 and avoid or reduce unwanted vacuum leaks. Additionally, the space between the vacuum line 320 and the cannula 240 can be reduced by crimping the exterior of the cannula 240.

In operation, when the stylet tip 310 is inserted into the target tissue, the cannula 340 may be moved forward at a relatively high speed to cover the stylet tip 310, and as a result sever a tissue sample from the body of the patient. For example, the cannula 340 may be fired forward via a spring which, when activated, may fire the cannula 340 forward to cover the stylet tip 310 and sever a tissue sample. According to various aspects, there are three different types of cannula firing mechanisms: i) manual, where the operator manually pushes the stylet tip 310 forward in the target tissue, and then manually pushes the cannula 340 forward to sever a tissue sample, ii) semi-automatic, where the operator manually pushes the stylet tip 310 forward in the target tissue, and then fires the cannula 340 forward via the spring or firing mechanism, and iii) automatic, where the operator fires both the stylet tip 310 and the cannula 340 forward into the target tissue via the spring or firing mechanism.

FIGS. 4A-4D are diagrams illustrating a communication between the vacuum line and the notch in a vacuum-assisted biopsy device, according to various aspects of the current invention. In FIG. 4A, the biopsy device 400 includes stylet tip 410 and a notch 450 connected to the vacuum line 420 located within the outer wall 440. According to various aspects, the notch 450 may be connected to the vacuum line 420 via a plurality of air/vacuum lines or microbores 465 that may be thinner than the vacuum line 420. In the example illustrated in FIG. 4A, two microbores 465 are illustrated, but those of ordinary skill in the art will recognize that more than two microbores 465 may be present to ensure air and/or vacuum communication between the notch 450 and the vacuum line 420. FIG. 4B illustrates a similar configuration as FIG. 4A, but with a single microbore 465 between the notch 450 and the vacuum line 420 to ensure air and/or vacuum communication.

In FIG. 4C, the biopsy device 400 includes the stylet tip 410 with the notch 450. According to various aspects of the current invention, the back portion of the stylet tip 410 may include a boss 475 that, in operation, may be fitted into a fitting 470, the fitting being insertable within the vacuum line 420. As a result, a vacuum or air communication may be established between the notch 450 and the vacuum line 420 so that the target tissue of a patient being subjected to the biopsy may be drawn in the notch 450 via the vacuum provided from the vacuum line 420, before and/or after being severed, according to various aspects. In addition, a plurality of pores 480 may be provided in the vacuum line to provide an alternative or additional path for the vacuum to the stylet tip 410.

In FIG. 4D, the back portion of the stylet tip 410 includes the boss 475, which, according to various aspects, may be directly inserted into the vacuum line 420. Accordingly, a vacuum or air communication may be established between the notch 450 and the vacuum line 420 so that the tissue sample of a patient being subjected to the biopsy may be drawn into the notch 450 via the vacuum provided via the vacuum line 420. According to various aspects, openings 485 may be provided in the vacuum line 420 to provide an alternative or additional vacuum path to the stylet tip 410 during insertion and operation of the biopsy device.

Figure 5B:
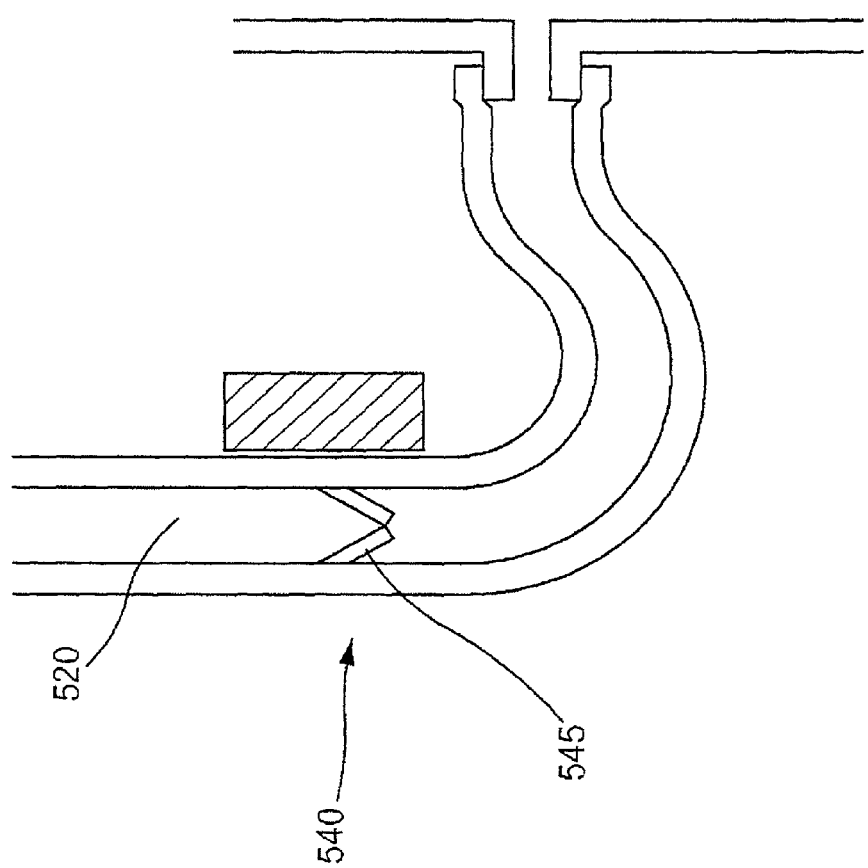

FIGS. 5A-5D are diagrams illustrating vacuum valves in a vacuum-assisted biopsy device, according to various aspects of the current invention. In FIG. 5A, a valve 570 includes a pinch valve, where a portion of the vacuum line 520 may be pinched in order to block or release passage of vacuum or air. FIG. 5B illustrates another type of valve 540 that is based on a duck bill 545, according to various aspects of the current invention. It should be noted that although the above valves have been illustrated, other types of valves may also be used to regulate the air or vacuum communication between the vacuum line 420 and the notch 450 in order to ensure a large draw of tissue sample into the notch 450 and provide larger tissue samples than the samples collected using conventional biopsy devices for biopsy analysis.

While aspects of this invention have been described in conjunction with the example features outlined above, various alternatives, modifications, variations, improvements, and/or substantial equivalents, whether known or that are or may be presently unforeseen, may become apparent to those having at least ordinary skill in the art. Accordingly, the example aspects of the invention, as set forth above, are intended to be illustrative, not limiting. Various changes may be made without departing from the spirit and thereof. Therefore, aspects of the invention are intended to embrace all known or later-developed alternatives, modifications, variations, improvements, and/or substantial equivalents.

What is claimed is:

1. A vacuum-assisted biopsy device, comprising:
    a stylet configured to incise tissue, the stylet including a notch defined by at least one wall; and
    a vacuum pump producing a vacuum pressure;
    a vacuum line comprising an annular wall and a lumen, the vacuum line in communication with the vacuum pump and a vacuum pathway, wherein the vacuum pathway is in communication with the vacuum line and the notch such that the vacuum line communicates the vacuum pressure from the vacuum pump through the lumen and the vacuum pathway to the notch along a first travel path; and
    at least one outlet or passageway extending completely through the annular wall of the vacuum line, the outlet or passageway being proximal to the notch and spaced from the notch, the at least one outlet or passageway arranged to be operable contemporaneously with the vacuum pathway to communicate the vacuum pressure from the vacuum pump when the notch is in contact with a tissue sample, and
    wherein the vacuum line is configured to communicate the vacuum pressure from the vacuum pump through the lumen and the outlet or passageway to the tissue sample along a second travel path such that the vacuum pressure is contemporaneously communicated along the first travel path and the second travel path, wherein the first travel path differs from the second travel path, and wherein the second travel path does not traverse the at least one wall defining the notch.

2. The vacuum-assisted biopsy device of claim 1, further comprising a valve configured to control the vacuum generated by the vacuum pump and transmitted to the notch.

3. The vacuum-assisted biopsy device of claim 1, further comprising one or more surface features located on an outside surface of the vacuum line.

4. The vacuum-assisted biopsy device of claim 1, wherein a back portion of the stylet comprises an elongated portion configured to fit into the vacuum line.

5. The vacuum-assisted biopsy device of claim 1, wherein an outer surface of the stylet is non-uniform.

6. The vacuum-assisted biopsy device of claim 5, wherein the outer surface of the stylet includes one or more depressions to allow vacuum movement around the outer surface of the stylet.

7. The vacuum-assisted biopsy device of claim 1, wherein:
    the vacuum line is enclosed within the outer wall of the biopsy device;
    a clearance separates an outer surface of the vacuum line with an inner surface of the outer wall; and
    a plurality of asperities located on the outside surface of the vacuum line, the asperities having a height equal to the clearance between the outer surface of the vacuum line and the inner surface of the outer wall; wherein
    a lubricant is provided in the clearance to form a vacuum membrane.

8. The vacuum-assisted biopsy device of claim 1, further comprising one or more bores inside a back portion of the stylet to provide a communication between the notch and the vacuum line.

9. The vacuum-assisted biopsy device of claim 1, further comprising a boss on a back portion of the stylet, wherein the boss includes a conduit, and is configured to fit within the vacuum line to connect the notch and the vacuum line.

10. The vacuum-assisted biopsy device of claim 9, wherein the biopsy device comprises a fitting in which the boss is fitted, the fitting including a conduit to connect the notch and the vacuum line.

11. The vacuum-assisted biopsy device of claim 2, wherein the valve is one of at least a pinch valve and a duck bill valve.

12. The vacuum-assisted biopsy device of claim 1, wherein the tissue sample is one of a human tissue sample and an animal tissue sample.

13. A vacuum-assisted biopsy device, comprising:
    a stylet configured to incise tissue, the stylet including a notch defined by at least one wall; and
    a vacuum pump producing a vacuum pressure; and
    a vacuum line comprising an annular wall and a lumen, the vacuum line in communication with the vacuum pump and a vacuum pathway, wherein the vacuum pathway is in communication with the vacuum line and the notch such that the vacuum line communicates vacuum pressure from the vacuum pump through the lumen and the vacuum pathway to the notch along a first travel path, and
    wherein an outer surface of the annular wall of the vacuum line comprises a plurality of projections having depressions therebetween, the plurality of projections having a uniform height and uniformly spaced along the vacuum line in a direction of vacuum flow; and
    at least one outlet or passageway extending completely through the annular wall of the vacuum line, the outlet or passageway being proximal to the notch and spaced from the notch, the at least one outlet or passageway arranged to be operable contemporaneously with the vacuum pathway to communicate the vacuum pressure from the vacuum pump when the notch is in contact with a tissue sample, and
    wherein the vacuum line is configured to communicate the vacuum pressure from the vacuum pump through the lumen and the outlet or passageway to the tissue sample along a second travel path such that the vacuum pressure is contemporaneously communicated along the first travel path and the second travel path, wherein the first travel path differs from the second travel path and wherein the second travel path does not traverse the at least one wall defining the notch.

14. The vacuum-assisted biopsy device of claim 1, wherein the vacuum pathway comprises a microbore.

15. A vacuum-assisted biopsy device, comprising:
    a stylet configured to incise tissue, the stylet including a notch defined by at least one wall;
    a vacuum pump;
    a vacuum line comprising an annular wall and a lumen, the vacuum line in communication with the vacuum pump and the notch, the vacuum line being in communication with the notch via a vacuum pathway such that the vacuum line communicates vacuum pressure from the vacuum pump through the lumen and the vacuum pathway along a first travel path to a portion of tissue via the notch; and
    an outlet or passageway extending completely through the annular wall of the vacuum line and which is spaced from the notch, wherein the outlet or passageway is arranged to be operable contemporaneously with the vacuum pathway to communicate the vacuum pressure from the vacuum pump when the notch is in contact with a tissue sample, wherein the vacuum line is configured to communicate the vacuum pressure from the vacuum pump through the lumen and the outlet or passageway to the tissue sample along a second travel path such that the vacuum pressure is contemporaneously communicated along the first travel path and the second travel path, wherein the vacuum pressure draws an additional portion of the tissue sample into the notch via the second travel path, wherein the first travel path differs from the second travel path, and wherein the second travel path does not traverse the at least one wall defining the notch.

\* \* \* \* \*